US010967021B2

(12) United States Patent
Purcell et al.

(10) Patent No.: US 10,967,021 B2
(45) Date of Patent: *Apr. 6, 2021

(54) ORAL COMPOSITIONS AND ROUTE OF ADMINISTRATION FOR THE DELIVERY OF A THYLAKOID EXTRACT

(71) Applicant: Groupe Santé Devonian Inc., Montmagny (CA)

(72) Inventors: Marc Purcell, Saint-Augustin-de-Desmaures (CA); Réjean Drouin, St-Gilles de Lotbinière (CA)

(73) Assignee: GROUPE SANTÉ DEVONIAN, Quebec (CA)

( * ) Notice: Subject to any disclaimer, the term of this patent is extended or adjusted under 35 U.S.C. 154(b) by 125 days.

This patent is subject to a terminal disclaimer.

(21) Appl. No.: 16/159,364

(22) Filed: Oct. 12, 2018

(65) Prior Publication Data

US 2019/0240276 A1 Aug. 8, 2019

Related U.S. Application Data

(60) Division of application No. 15/342,807, filed on Nov. 3, 2016, now Pat. No. 10,124,029, which is a continuation of application No. 14/489,731, filed on Sep. 18, 2014, now Pat. No. 9,555,068, which is a continuation of application No. 12/171,927, filed on Jul. 11, 2008, now abandoned, which is a continuation of application No. 10/573,139, filed as application No. PCT/CA2004/001724 on Sep. 22, 2004, now abandoned.

(60) Provisional application No. 60/503,881, filed on Sep. 22, 2003.

(51) Int. Cl.
| | |
|---|---|
| *A61K 36/00* | (2006.01) |
| *A61K 36/21* | (2006.01) |
| *A23L 33/105* | (2016.01) |
| *A61K 9/00* | (2006.01) |

(52) U.S. Cl.
CPC ............ *A61K 36/21* (2013.01); *A23L 33/105* (2016.08); *A61K 9/0053* (2013.01); *A61K 36/00* (2013.01); *A23V 2002/00* (2013.01)

(58) Field of Classification Search
CPC .................................................... A61K 36/00
See application file for complete search history.

(56) References Cited

U.S. PATENT DOCUMENTS

| | | | | |
|---|---|---|---|---|
| 4,976,960 | A | * | 12/1990 | Grossman ............. A23L 3/3463 424/451 |
| 2003/0108593 | A1 | | 6/2003 | Oku et al. |
| 2003/0143276 | A1 | | 7/2003 | Hsia et al. |
| 2003/0175374 | A1 | | 9/2003 | Purcell |
| 2003/0225003 | A1 | | 12/2003 | Ninkov |
| 2005/0048148 | A1 | | 3/2005 | Anderson et al. |

FOREIGN PATENT DOCUMENTS

| | | |
|---|---|---|
| CA | 2293852 | 6/2001 |
| JP | 2003/160495 | 6/2003 |
| JP | 2003/183176 A | 7/2003 |
| WO | WO 01/049305 A2 | 7/2001 |
| WO | WO 0149305 A2 * | 7/2001 |
| WO | WO 03/004042 A1 | 1/2003 |

OTHER PUBLICATIONS

"Nutraceutical" from Dictionary.com, accessed on Feb. 5, 2009, pp. 1-3. (Year: 2009).*

(Continued)

*Primary Examiner* — Qiuwen Mi
(74) *Attorney, Agent, or Firm* — Hahn Loeser & Parks, LLP (57) ABSTRACT

The present invention provides a new use or method of use of a thylakoid extract, for oral route of administration, and a composition comprising the thylakoid extract in adjunction with an acceptable carrier for oral administration. Besides the pharmaceutical use, the thylakoid extract enters the composition of food or food supplements, or medication for its innocuity and its capacity to provide a diet enriched in anti-oxidants and anti-inflammatory compounds. Therefore, in accordance with the present invention is provided the use of athylakoid extract in the making of an oral composition for treating preventing a disease or disorder involving the formation of reactive oxygen species or inflammation. Also is provided a method for treating or preventing a disease or disorder involving the formation of reactive oxygen species inflammation in an individual, which comprises the step of orality administering an effective dose of a thylakoid extact. Further is provided an oral composition comprising a thylakoid extract and a vehicle for oral ingestion or oral administration. An oral composition comprising purified thylakoids and a carrier for oral ingestion or oral administration, with the proviso that the carrier does not essentially consists of water, physiological saline or propylene glycol is also provided as food or a food supplement, or as a peliet, or encapsulated granules or powder. The carrier may be present in an amount of 0.01% to 95% (w/w) of the total composition. The purified thylakoids are present in an amount which achieves a dosage of 0.1 to 10 mg per Kg of a subject's body weight.

10 Claims, 6 Drawing Sheets

(56) References Cited

OTHER PUBLICATIONS

International Search Report and Written Opinion of the International Searching Authority from PCT/CA2004/001724 dated Feb. 14, 2005.
Jan. 11, 2008 Office Action in connection with U.S. Appl. No. 10/573,139.
Apr. 17, 2009 Office Action in connection with U.S. Appl. No. 12/171,927.
Supplemental European Search Report from European Application No. 04786644.7 dated Jul. 6, 2009.
Sep. 29, 2009 Office Action in connection with U.S. Appl. No. 12/171,927.
Notification of Reasons for Refusal, Japan Patent Application No. 2006-526498 (dated Mar. 9, 2010).
Sep. 4, 2013 Office Action in connection with U.S. Appl. No. 12/171,927.
Mar. 18, 2014 Office Action in connection with U.S. Appl. No. 12/171,927.
Third Party Submission under 37 CFR 1.290 in U.S. Appl. No. 14/489,731 (dated Jun. 20, 2015).
Aug. 11, 2016 Office Action in connection with U.S. Appl. No. 14/489,731.
Apr. 10, 2018 Office Action in connection with U.S. Appl. No. 15/342,807.
Bissonnette, et al., "PCT-233, A novel modulator of pro- and anti-inflammatory cytokine production," *Clin. Exp. Immunol*, 135:440-447 (2004).
Boughton-Smith, et al. "Role of oxygen radicals and arachidonic acid metabolites in the reverse passive Arthus reaction and carrageenin paw oedema in the rat," *BR. J. Pharmacol*, 110:896-902 (1993).
Christen, et al. "P680+ Reduction Kinetics and Redox Transition Probability of the Water Oxidizing Complex as a Function of pH and H/D Isotope Exchange in Spinach Thylakoids" *Biochemistry*, 1999, 38(19), pp. 6082-6092. DOI: 10.1021/bi9827520.
Gasanov R., et al., "Comparative study of the water oxidizing reactions and the millisecond delayed chlorophyll fluorescence in photosystem II at different pH." *J Photochem Photobiol B*. Feb. 1, 2007; 53(2):160-4.
Ziya Al-Din Abdullah Ibn Al-Baitar, *Al-Jaam'e-li-Mufradaat-al-Advia-wal-Aghzia*, (vol. 1 pp. 4-8, Matba Amra, Cairo, Egypt 1874).
Jajoo A, et al. "Low pH induced structural reorganization in thylakoid membranes." *Biochim Biophys Act*. Aug. 2012; 1817(8):1388-91. Doi:10.1016/j.bbabio.2012.01.002.
Kamb, "What's wrong with our cancer models?" *Nature Reviews* 4:161-165 (2005).
Mohammad Najmul Chani Khan, *Khazaain-al-Advia*, pp. 9-14 (Sheikh Mohd Basheer & Sons, Lahore, India 1911).
Lemieux, et al. "Properties of Immobilized Thylakoid Membranes in a Photosynthetic Photoelectrochemical Cell" *Photochem Photobiol.*, 48 (1): 115-121 doi.org/10.111/j.1751-1097.1988.tb02795.x.
Lichtenthaler, "Chlorophylls and Carotenoids: Pigments of Photosynthetic Biomembranes," *Methods in Enzymology*, 148: 350-382 (1987).
Maxwell, et al., "Chlorophyll fluorescence-a practical guide" *Journal of Experimental Botany*, vol. 51 (345): 659-668 (2000).
Chikahiro Miyake "Gastrointestinal Disorders and Active Oxygen/ Free Radicals: Toxicity of Active Oxygen and Protection Mechanism Against Oxidative Stress" *Clinical Gastroenterology*, Japan, 1995, Oct. 6, pp. 745-754.
Waris, et al., "Reactive oxygen species: role in the development of cancer and various chronic conditions," *Journal of Carcinogenesis* 5(14):1-8 (2006).
Yamamoto et al., "Anti-inflammatory Action of Orally Active 5-Lipoxygenase Inhibitor TMK688," *Pharmacology*, 48:273-282 (1994).
*Journal of Pharmaceutical Sc.* vol. 52, p. 918 et seq. (1963).
"Nutraceutical" from Dictionary.com, pp. 1-3, accessed on Feb. 29, 2009.
*U.S. Pharmacopeia National Formulary*, USP CCII, NP XVII, p. 1789 (US Pharmacopeial Convention Inc., Rockville, MD 1990).

\* cited by examiner

ORAL COMPOSITIONS AND ROUTE OF ADMINISTRATION FOR THE DELIVERY OF A THYLAKOID EXTRACT

This application is a divisional of U.S. application Ser. No. 15/342,807 filed 3 Nov. 2016, which is a continuation of U.S. application Ser. No. 14/489,731 filed 18 Sep. 2014, which is a continuation of U.S. application Ser. No. 12/171,927 filed 11 Jul. 2008, which is a continuation of U.S. application Ser. No. 10/573,139 filed 22 Mar. 2006, which is a § 371 U.S. National Stage of International Application No. PCT/CA2004/001724 filed 22 Sep. 2004, which was published in the English language and published on 31 Mar. 2005 with International Publication No. WO 2005/027944 A1 and which claims the benefit of the filing date of U.S. application Ser. No. 60/503,881 filed 22 Sep. 2003. All of these applications are incorporated herein by reference in their entirety.

FIELD OF THE INVENTION

This invention relates to oral administration of a thylakoid extract or of compositions comprising same.

BACKGROUND OF THE INVENTION

Thylakoids are specialized membranes that are responsible for photosynthesis in eukaryotes (plant & algae) and prokaryotes cells (bacteria). These photosynthetic organisms convert $CO_2$ to organic material by reducing this gas to carbohydrates in a complex set of reactions. Electrons for this reduction reaction ultimately come from water, which is then converted to oxygen and protons. Energy for this process is provided by light, which is absorbed by pigments (primarily chlorophylls and carotenoids).

The initial electron transfer (charge separation) reaction in the photosynthetic reaction center sets into motion a long series of redox (reduction-oxidation) reactions, passing the electron along a chain of cofactors and filling up the "electron hole" on the chlorophyll, much like in a bucket brigade. All photosynthetic organisms that produce oxygen have two types of reaction centers, named photosystem I & photosystem II (PSI and PSII) both, of which are pigment/protein complexes that are located in thylakoids membrane.

Recently a dynamic and intact thylakoid membrane extract having both anti-oxidative and anti-inflammatory properties and its use in combination with other anti-inflammatory compounds have been described in International patent publication numbers WO 01/49305 and WO 03/04042, respectively. The anti-oxidative and anti-inflammatory properties of the thylakoid extract have been demonstrated in in vitro, ex vivo, in situ and in vivo studies. Specifically, the thylakoid extract has been shown to capture the noxious reactive oxygen species including singlet oxygen species and to modulate pro- and anti-inflammatory cytokines toward attenuation of inflammation.

In vivo, topical applications (direct application at site of injury) of the thylakoid extract have been shown to prevent or reduce the UV-induced skin damages in hairless mice and to decrease TPA-induced ear inflammation in rats and mice as well as preventing damage to intestinal mucosa induced by TNBS or DSS in rats. Also, intraperitoneal injection of the thylakoid extract has been shown to reduce carrageenan-induced paw oedema. However, today, no data has confirmed the potential use of the thylakoid extract as an oral anti-oxidative and/or anti-inflammatory agent.

The present invention relates to the use of a thylakoid extract as an oral therapeutic agent.

SUMMARY OF THE INVENTION

The present invention provides a new use for a thylakoid extract, that is for oral route of administration, and a composition comprising the thylakoid extract in adjunction with an acceptable carrier for oral administration. Besides the pharmaceutical use, the thylakoid extract enters the composition of food or food supplements, for its innocuity and its capacity to provide a diet enriched in anti-oxidants and anti-inflammatory compounds.

Therefore, in accordance with the present invention is provided the use of a thylakoid extract, in the making of an oral composition for treating or preventing a disease or disorder involving the formation of reactive oxygen species or inflammation. Also is provided a method for treating or preventing a disease or disorder involving the formation of reactive oxygen species or inflammation in an individual, which comprises the step of orally administering an effective dose of a thylakoid extract. Further is provided an oral composition, comprising a thylakoid extract and a vehicle for oral ingestion or oral administration.

Therefore, in accordance with the present invention is provided a use of purified thylakoids in the making of an oral composition for treating or preventing a disease or disorder involving the formation of reactive oxygen species or inflammation.

Further is provided the use of purified thylakoids in the making of an oral composition for preventing oxidative damages to components of the composition. In a specific embodiment, the oral composition is food or a food supplement. In another embodiment, the oral composition is a medication against oxidative damages, disorders or diseases.

Also is provided a method for treating or preventing a disease or disorder involving the formation of reactive oxygen species or inflammation, in a subject, which comprises the step of orally administering an effective dose of purified thylakoids.

An oral composition comprising purified thylakoids and a carrier for oral ingestion or oral administration, with the proviso that the carrier does not essentially consist of water, physiological saline or propylene glycol is also provided as food or a food supplement, or a medication in the form of a pellet, encapsulated granules or encapsulated powder.

The carrier may be present in an amount of 0.01% to 95% (w/w) of the total composition.

The purified thylakoids are present in an amount which achieves a dosage of 0.1 to 10 mg per Kg of a subject's body weight.

DESCRIPTION OF THE INVENTION

Demonstration will be made hereinbelow that the thylakoid extract (hereinbelow also referred to as "purified thylakoids" or "PCT") is active when orally administered. The extract can be formulated as a liquid composition (a non-lyophilized extract), a lyophilized extract reconstituted in water, physiological saline or any other solution compatible with oral administration, in propylene glycol (100% or lower concentrations) or as a solid composition (as is or in adjunction with pharmaceutically acceptable carrier for oral administration). Thylakoids compositions essentially consisting of lyophilized thylakoids, thylakoids reconstituted in water or in saline as well as thylakoids purified and obtained in propylene glycol have been disclosed in WO 01/49305, although their use for oral administration was not disclosed in this reference.

The contents of all cited documents are incorporated by reference.

Excipients and carriers are widely used in the pharmaceutical field and are known to those skilled in the art. Amongst them, binding agents, disintegrating agents and/or fillers are of current use. The form taken by the product may also vary widely. Dry products comprise pellets, and powders and granules in a free form or in capsules. Liquid products may comprise lipids (oils and fats), stabilizers, emulsifiers, surfactants, polymers, and/or any colorant or flavoring additive to improve the taste, the scent or the appearance of the composition.

Examples of binding agents include gelatine, cellulose, cellulose ethers, amyloses, dextrose, polyglycols, tragacanth, pectins, alginates and polyvinyl pyrrolidone (PVP).

Examples of disintegrating agents include starches, modified starches (sodium starch glycolate starch 1500, . . . ) pectins, betonite, cellulose, cellulose derivatives like carboxymethylcellulose (CMC), alginates, PVPs, ultraamylopectin, crosslinked PVP or crosslinked CMC (such as Ac-Di-Sol/FMC).

Examples of fillers include lactose, glucose, fructose, calcium phosphates, sulfates or carbonates, starch, modified starch, sugar alcohols such as sorbitol and mannitol, cellulose derivatives, saccharose, and/or microcrystalline cellulose.

Several types and selections of auxiliary substances forming carriers for oral use are described for example in *Journal of Pharmaceutical Sc.* (1963), vol 52, from p. 918 and following.

Preparation of Spheroids Comprising Plant Material is Described in U.S. Pat. No. 5,733,551.

In general, the amount of active ingredient, that is the thylakoids, can extend from 1 µg to 1 g per day in one or more doses. In humans, a range of doses of 0.1 to 10 mg per Kg of body weight appears to be suitable. Therefore, for an averaged 70 Kg subject, a 5-10 mg to 500-1000 mg daily dosage regimen would be adequate. Examples of 200 mg pellets comprising 20, 40 and 60% (40, 80 and 120 mg) thylakoids have been made and are described hereinbelow. Pellets of 200 to 300 mg can be also made of pure compressed thylakoids (without any auxiliary agents).

This invention will be described herein below referring to specific examples, embodiments and figures, the purpose of which is to illustrate the invention rather than to limit its scope.

EXAMPLE 1: THE THYLAKOIDS ARE ACTIVE AS ENTERAL AND ORAL COMPOUNDS

Methodology

Animals

Male Wistar rats (180-200 g) were used in the experiments. The animals were purchased from Charles River Canada (St-Constant, Qc, Canada). The animals were housed in an environmentally (t=25° C.) and air humidity (60%) controlled room with a 12 h light-dark cycle, kept on a standard laboratory diet and drinking water ad libitum. The experiments were approved by the ethical committee of TransBIOTech (Levis, Qc, Canada).

Reagents

12-O-tetradecanoyl phorbol 13-acetate (TPA, P-8139) and carrageenan (C-1138) were purchased from Sigma Chemical Co. (St-Louis, Mo. USA).

Preparation of the Thylakoid Extract

The thylakoid extract was obtained from spinach leaves (Spinacia oleacea) as described in international patent publication WO 01/49305, the whole content of which is incorporated herein by reference. The thylakoids integrity was evaluated by spectrophotometry (Beckman DU 640) (Lichtenthale 1987) and fluorimetry (Hansatech Instruments Ltd, England) (Maxwell 2000).

Protocol 1: TPA-Induced Rat Ear Oedema

Male Wistar rats (180-200 g, Charles River) were fasted overnight (18 h). Oedema was induced in the right ear of rats by topical application of 6 µg/ear of TPA in acetone (Yamamoto S et al. 1994). The left ear (control) received vehicle (acetone, 20 µl).

Six hours after TPA application, rats were anesthetized (pentobarbital; 80 mg/kg) and a 6 mm diameter disc from each ear was removed with metal punch. The swelling induced by TPA was assessed as the increase in thickness (in mm) of the right ear punch biopsy over that of the left ear and called the oedema index.

The thylakoid extract (25 mg/kg) was administered directly to the duodenum (5 ml/kg) via a catheter previously inserted into the duodenum. Physiology saline was administered for control groups (5 ml/kg).

Protocol 2: Carrageenan-Induced Rat Paw Oedema

Male Wistar rats (180-200 g) which had been fasted overnight (18 h) received the thylakoid extract (25 mg/kg in sterile physiologic saline) by gavage (5 ml/kg) immediately prior to sub-plantar injection in the right hind paw of carrageenan (100 µl of 1% suspension in 0.9% saline) (Boughton-Smith et al. 1993), or by catheter for an in situ release as in protocol 1.

Paw circumference was measured immediately prior to carrageenan injection and also 5 h afterwards. Oedema was expressed as the increased in paw circumference (in mm) measured after carrageenan injection and compared to the pre-injection value for individual animals.

Statistical Analysis

Data are presented as mean±standard error of the means. Mean differences between groups were compared by t-test (SigmPlot 2001 for Windows Version 7.101).

Results

Effect of Thylakoids on TPA-Induced Ear Oedema in Rats.

Figure 1:
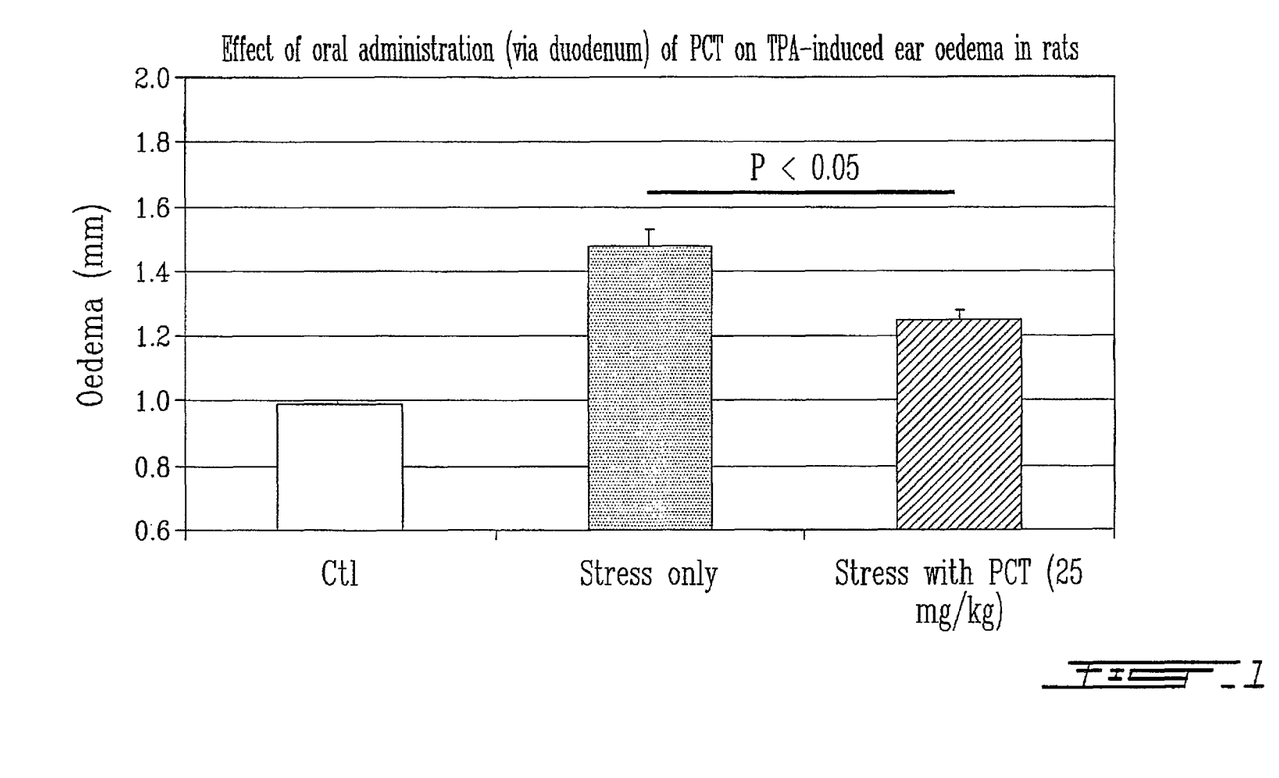
FIG. 1 shows the effect of enteral administration of thylakoids on TPA-induced ear oedema.

Topical application of TPA in control rats induced an increase in ear thickness (50%) over 6 h (FIG. 1). Simultaneous administration of thylakoids (25 mg/kg given directly into the duodenum via an inserted catheter) reduced (45%) significantly ear oedema induced by TPA.

Effect of Thylakoids on Carrageenan-Induced Rat Paw Oedema

Figure 2:
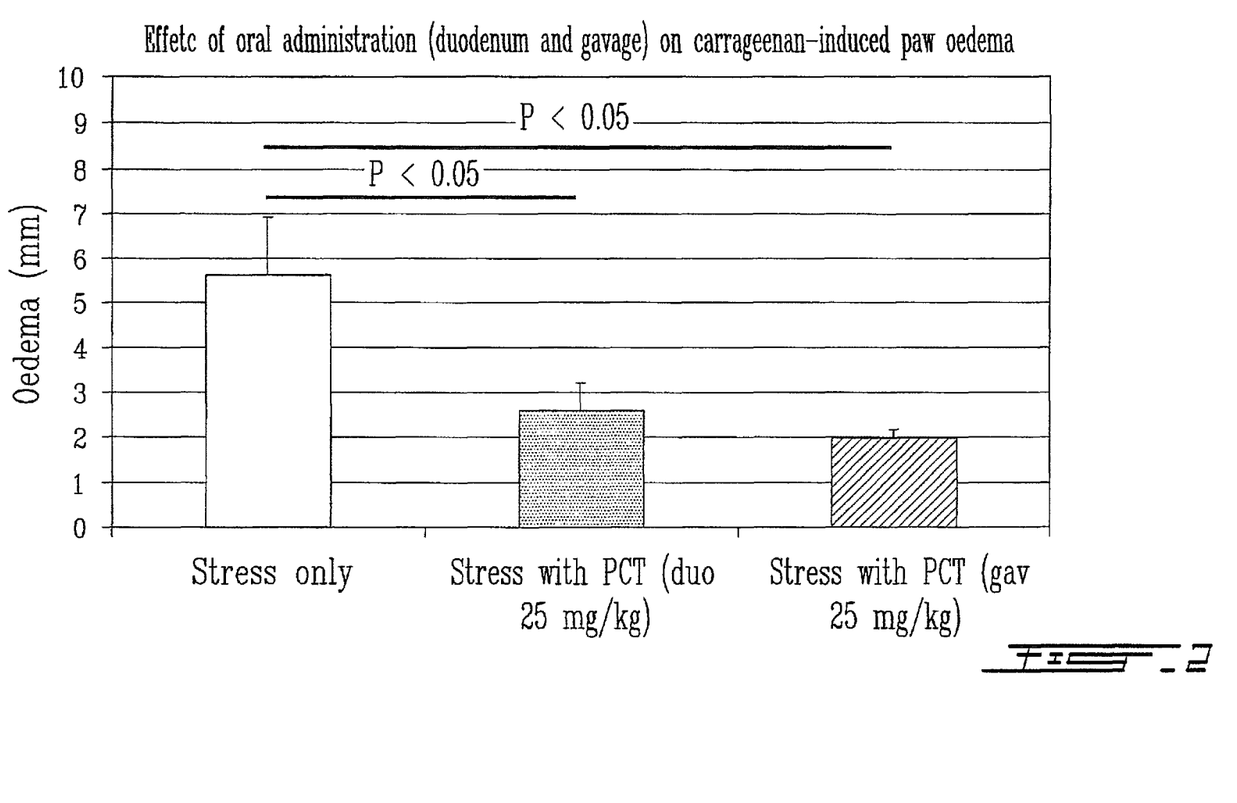
FIG. 2 shows the effect of enteral and oral administration of thylakoids on carrageenan-induced paw oedema.

The sub-plantar injection of carrageenan in control rats induced an increase in paw circumference (5.63±1.29) over 5 h (FIG. 2). Simultaneous treatment with the thylakoid extract (25 mg/kg) directly into duodenum via a previously inserted catheter or by gavage (5 ml/kg), inhibited oedema by 54% and 65%, respectively.

The above results show that the thylakoid extract can be administered enterally or orally. In inflammation models like TPA-induced rat ear oedema and carrageenan-induced rat paw oedema, a decrease of oedema of about 50% was observed at a dose of 25 mg/kg. Thus it is presumed that a dose of 10 to 10000 mg p.o. per day of thylakoids could be used alone or in combination with any other adjuncted pharmaceutical compound. The intended use is pharmaceutical as well as in food industry as food supplement, additive, preservative or as nutrient per se.

EXAMPLE 2: THE THYLAKOID EXTRACT CAN BE FORMULATED AS A PRODUCT FOR ORAL USE

Materials and Methods
Materials

Three commercially available polymers were used for this study sodium alginate, carboxymethyl cellulose low viscosity (CMC1) and carboxymethyl cellulose high viscosity (CMC2). The complex PCT was given by PureCell Technologies inc.
PCT Stability to Compression First of all, PureCell Technologies Inc. PTC was compressed as such, with any excipient, in order to evaluate the capacity of PCT to preserve its biological activity, following compression. Tablets of 200 mg made from PCT only were obtained by dry compression at 1, 2.5 and 5 T in a Carver hydraulic press using a punch of 9 mm diameter. The obtained tablets were broken down to powder and sent to PureCell Technologies Inc. where the complex activity was tested.
PCT Stability to Compression in Presence of Polymeric Excipients Tablets of 200 mg based on, one of the three polymers (alginate, CMC1 or CMC2) containing 20, 40 or 60% of PCT were obtained by dry compression at 2.5 T in a Carver hydraulic press using a punch of 9 mm diameter. The obtained tablets were sent to PureCell Technologies Inc. where the complex activity was tested.
Tablet Behavior in Simulated Gastro-Intestinal Fluid Two series-of tablets of 200 mg were realized, one composed of one of the three polymers (alginate, CMC1 or CMC2) without the PCT and the other based on one of the three polymers containing 20, 40 or 60% of PCT. Tablets were obtained by dry compression at 2.5 T in a Carver hydraulic press with a 9 mm diameter punch.

The comportment of tablets was tested in simulated gastric fluid (SGF) and in simulated intestinal fluid (SIF). These medium were prepared according to U.S. Pharmacopeia (1990) with the difference that we omitted the addition of pepsin and pancreatin because none of the polymers tested can be hydrolyzed by these enzymes. The medium were prepared as follow:

For SGF an amount of 2 g sodium chloride and of 7 mL HCl (37%) were dissolved in sufficient water to make 1 L.

For SIF an amount of 6.8 g of monobasic potassium phosphate was dissolved in 250 mL of water and a volume of 190 mL, of 0.2 N sodium hydroxide was added to the solution to adjust pH at 7.5. Then, the solution was completed to 1 L to obtain the simulated intestinal fluid solution.

Figure 3:
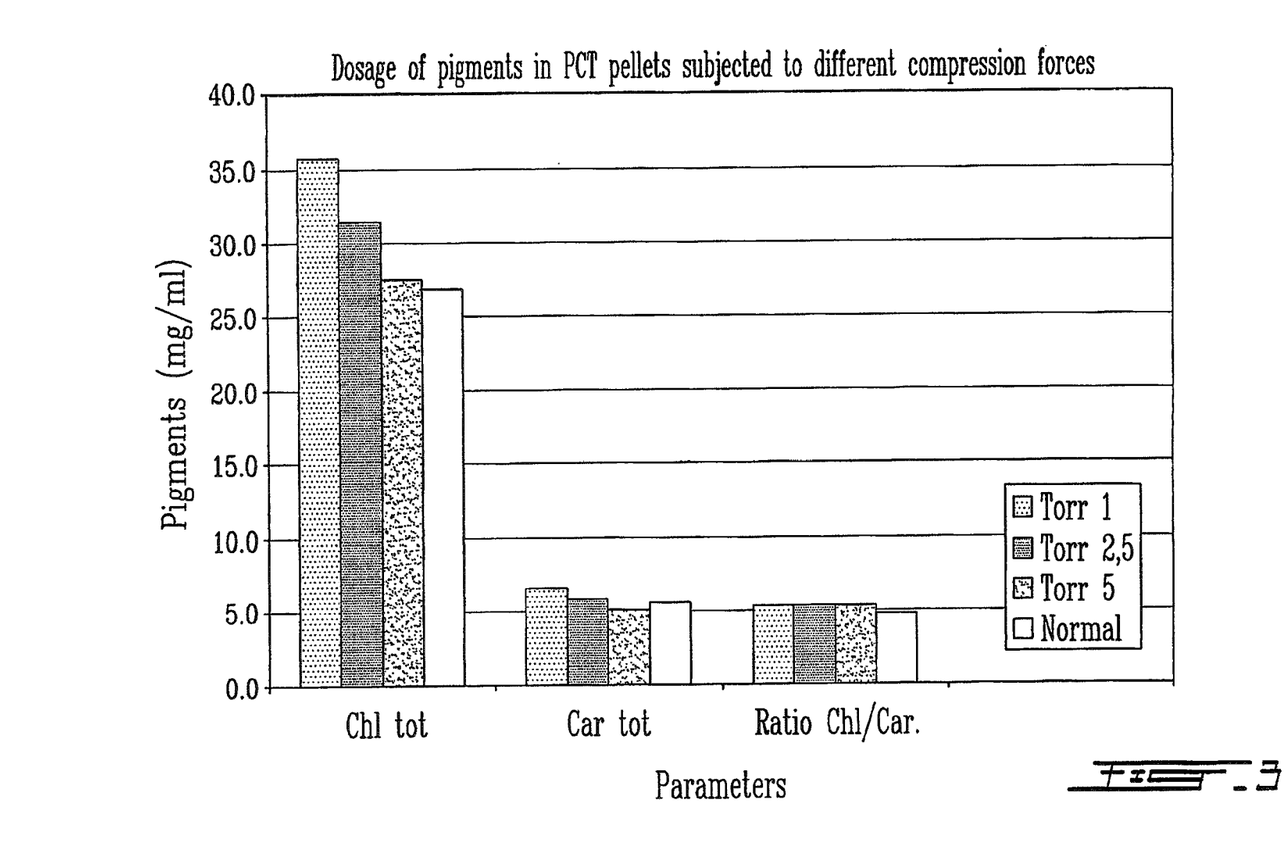
FIG. 3 represents the dosage of pigments to evaluate the pigment integrity following the compression of thylakoids at different pressures.

Practically for gastrointestinal comportment, tablets were placed in 50 mL of SGF for 1 hour and then in 50 mL, of SIF for 5 hours. The tablet's behavior was evaluated after each hour (glass adhesion, swelling, dissolution).
Results
PCT Stability to Compression There is no effect of the compression force on the membrane integrity. The total carotene contents and the total chlorophyll contents were the same and, as results, the ratio chlorophyll/carotene was unchanged (FIG. 3).

Figure 4:
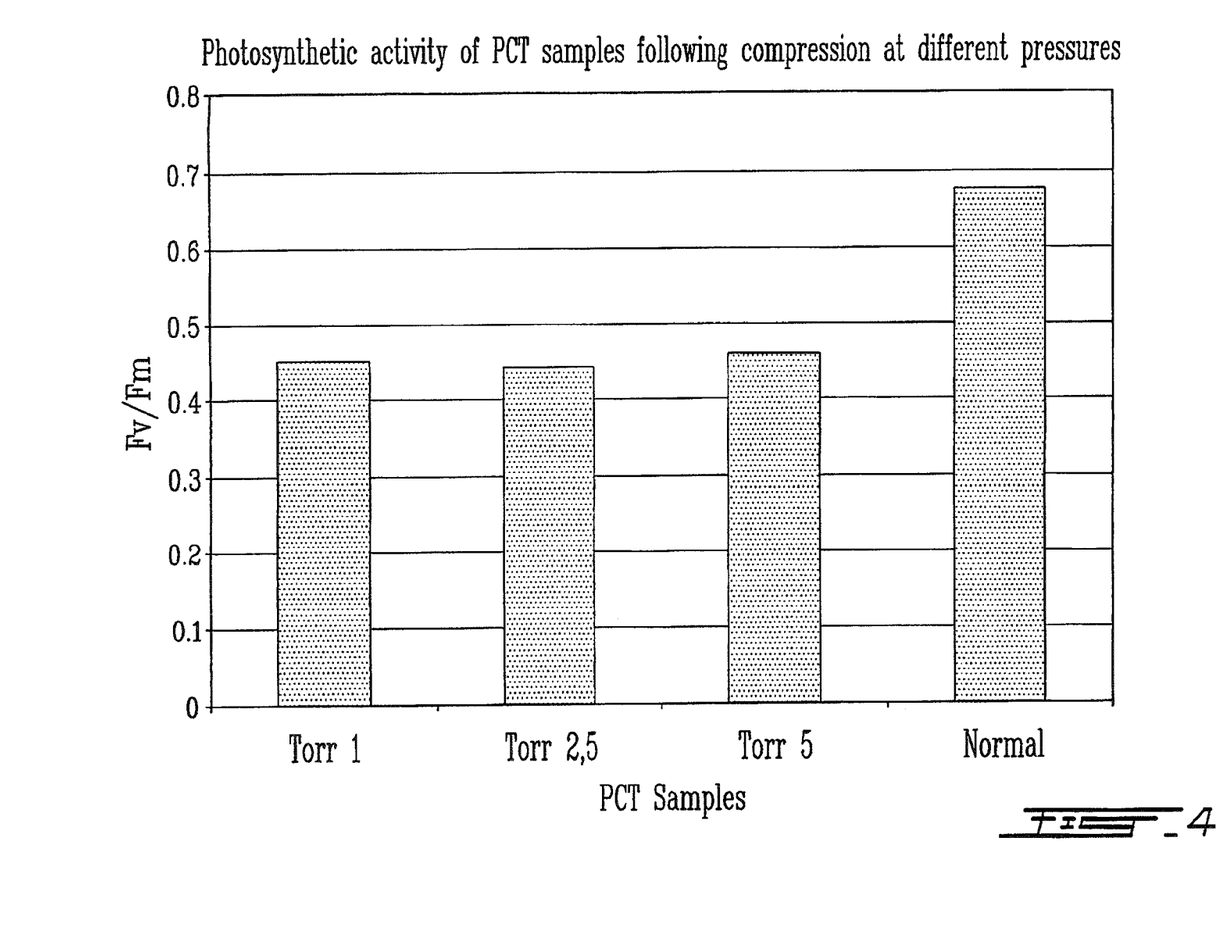
FIG. 4 shows the photosynthetic activity of the thylakoids following compression at different pressures.
Figure 5:
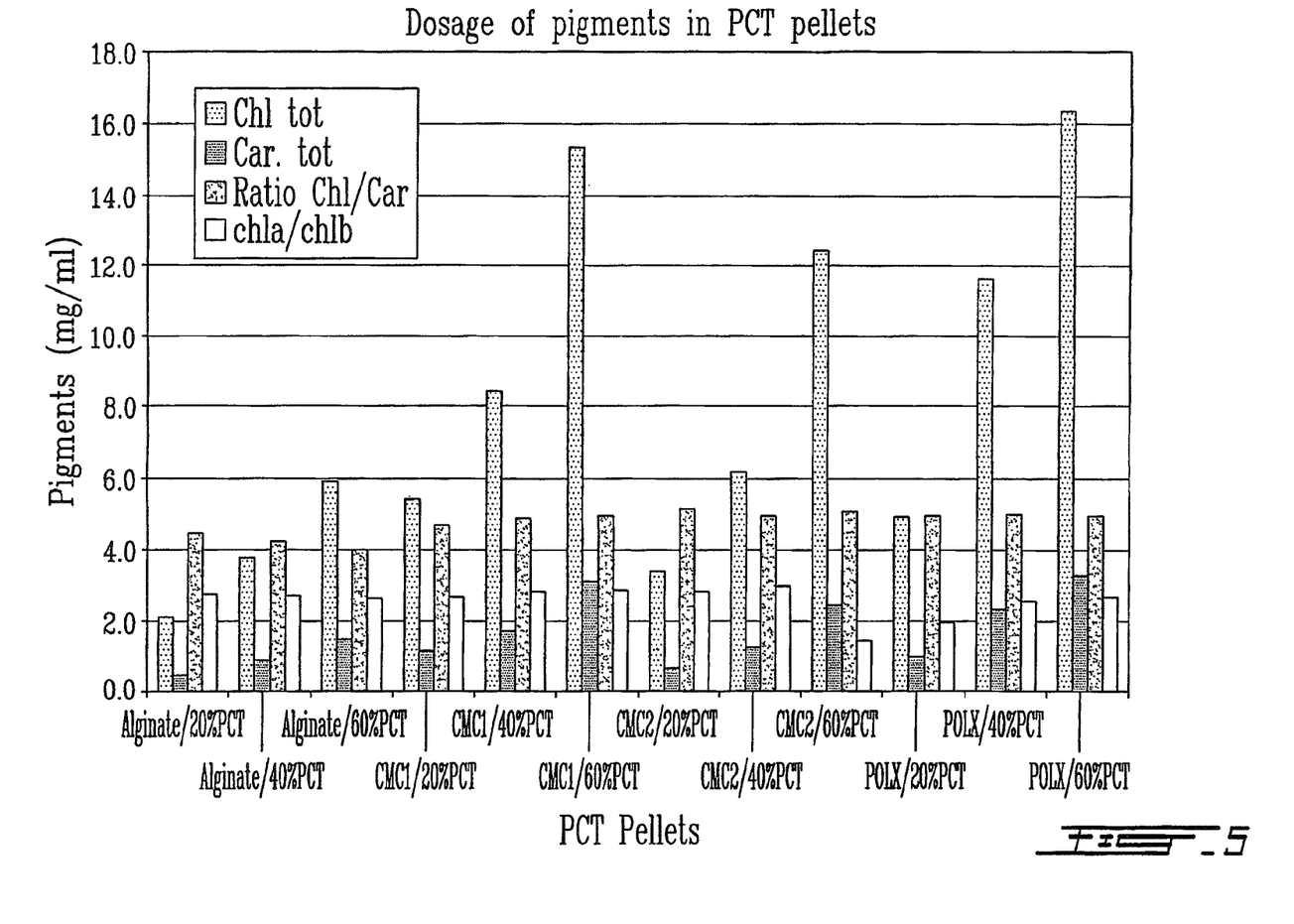
FIG. 5 shows the pigment integrity of the thylakoids following compression in the presence of diverse polymers.

The photosynthetic activity of the PCT was moderately affected by the compression in fact about 35% of the activity was lost during the compression with the mention that compression force do not seems to affect the activity (FIG. 4).
PCT Stability to Compression in Presence of Polymer The variation of the carotene and chlorophyll contents was proportionally increased with the PCT contents of the tablet and in each case the ratio chlorophyll/carotene was unchanged. On the other side, there is a variation of the amount of pigment determined in tablet having the same amount of PCT but formulated with different polymers (FIG. 5). In fact, for CMC1 a higher amount of pigments was detected than for CMC2, for which a higher amount of pigments than for alginate was detected.

It appears that alginate led to lower amounts of pigments than CMC excipients. As a possible explanation, the higher adhesive capacity of alginate can retain part of the pigments, or disturb the assay. Among CMC excipients, CMC1 (low viscosity) led to highest amounts of pigments detected. Same effect of higher pigments retention on high viscosity CMC2 can explain this behaviour. However, differences among polymeric excipients are much lower in terms of total carotenoids, Chla/Chlb and Chl/Car ratio.

Figure 6:
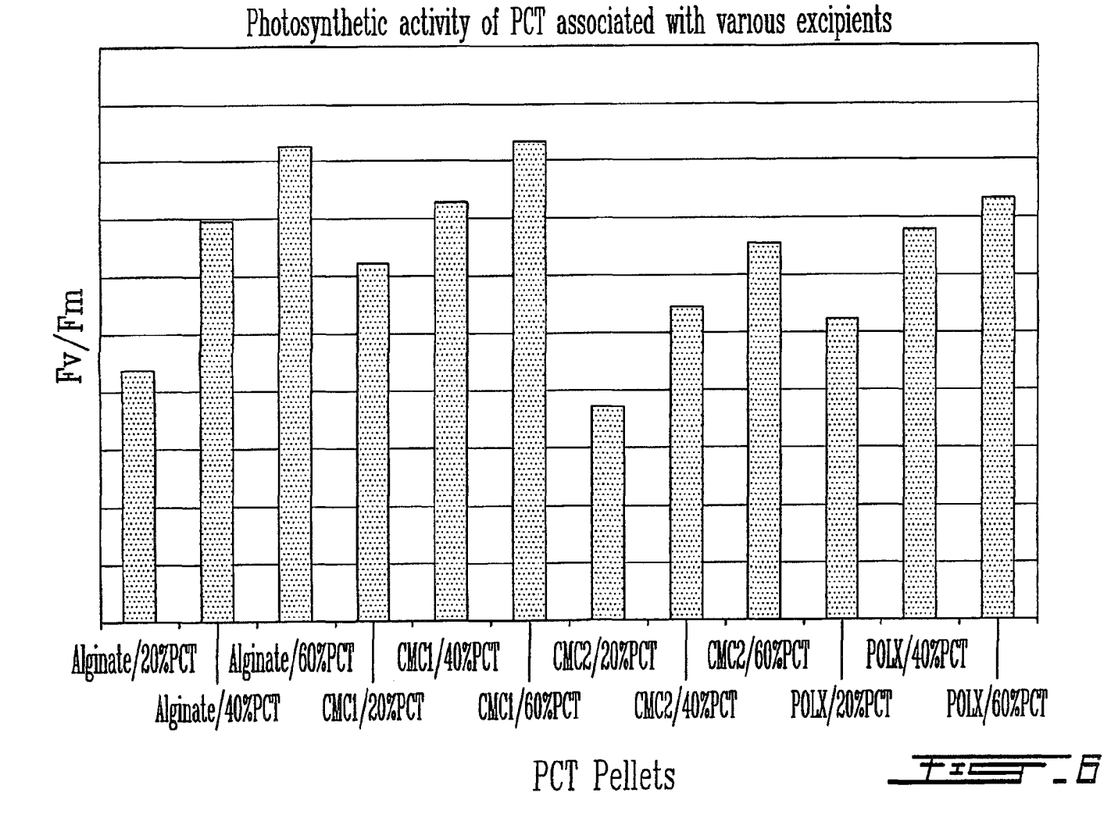
FIG. 6 shows the effect of various concentrations of thylakoids in diverse polymers on the thylakoids synthetic activity.

Concerning the photosynthetic activity, for tablet containing 20% PCT CMC1 conserved more activity following by alginate and CMC2 in decreasing order. The activity increase was not strictly proportional but the growing was continuous with tablet contains. It looks like the PCT contents increased from 20% to 40 and 60% moderately increased the photosynthetic activity (FIG. 6).
Tablet Behaviour in Simulated Gastrointestinal Fluid The behaviour of tablets composed of polymers only is presented in table 1. During one hour incubation in SGF, alginate and CMC1 polymeric matrices have a slight swelling and stick to the glass, whereas CMC2, which sticks to the glass too, have a higher swelling volume. After one hour in SIF, all the polymeric tablets were surrounded by a gel and remained adhering to the glass. During the four next hours in SIF, the different types of tablets were always adhered to the glass. Alginate continuing to swell, it start to dissolve after 4 hours in SIF and does not totally form a gel, even after 5 hours. CMC1 start to dissolve after only 2 hours in SIF; after 5 hour its dissolution was very advanced and it was completely under gel form. CMC2 have the highest swelling volume and was completely under gel form but does not seem to dissolve. Other auxiliary agents are to be added to improve CMC2 pellets dissolution.

The behaviour of tablets containing 20, 40 or 60% of PCT was similar to those of the corresponding polymer without PCT. An additional observation was the liberation in SIF of the green PCT. With alginate there is few PCT release which is not significantly increased at higher PCT loading. CMC2 forms a highly swollen gel, which releases few amounts of PCT and the release increased with the increase of PCT tablet loading. CMC1 dissolution helped the release of PCT, which is practically totally released in 5 hours. Auxiliary agents may be added to modulate the pellet dissolution, rate and time, and the thylakoids release.

The invention being hereinabove described, it will be obvious that the same be varied in many ways. Those skilled in the art recognize that other and further changes and modifications may be made thereto without departing from the spirit of the invention, and it is intended that all such changes and modifications fall within the scope of the invention, as defined in the appended claims.

TABLE 1

Tablets behavior during the incubation in simulating gastric fluid (SGF) and simulated intestinal fluid (SIF)

| | | 1 hour SGF | 1 hour SIF | 2 hours SIF | 3 hours SIF | 4 hours SIF | 5 hours SIF | over-night |
|---|---|---|---|---|---|---|---|---|
| Alginate | Glass adhesion | yes | yes | yes | yes | yes | yes | yes |
| | | no | no | around | around | around | | |
| | Gel aspect | around | low | low | + | + | | |
| | Swelling | no | no | no | no | begin | | |
| | Tablets dissolution | | | | | | close to totally + partially | totally + totally |
| CMC 2 | Glass Adhesion | yes | yes | yes | yes | yes | yes | yes |
| | | no | around | around | around | | | totally |
| | Gel aspect | + | ++ | ++ | ++ | | | ++ |
| | Swelling | no | no | no | no | | | no |
| | Tablets dissolution | | | | | close to totally ++ no | totally ++ no | |
| CMC 1 | Glass Adhesion | yes | yes | yes | yes | yes | yes | yes |
| | | around | around | around | | | | totally |
| | Gel aspect | "hat" | low | + | | | | + |
| | Swelling | no | no | begin | | | | totally |
| | Tablets dissolution | | | | close to totally + begin | totally + partially | close to totally + partially | |

REFERENCES

Yamamoto S, Jiang H, Kato R. Anti-inflammatory action of orally active 5-lipoxygenase inhibitor TMK688. *Pharmacology* 1994; 48:273-82.

Boughton-Smith N K, Deakin A M, Follenfant R L, Whittle B J, Garland L G. Role of oxygen radicals and arachidonic acid metabolites in the reverse passive Arthus reaction and carrageenin paw oedema in the rat. *Br J Pharmacol* 1993; 110:896-902.

Purcell M. (1999), Procedure for preparing active plant extracts used to trap free radicals; the extracts and compounds and devices containing them. Canadian patent CA 2293852.

Lichtenthaler K. K. (1987), Chlorophylls and carotenoids: Pigments of Photosynthetic Biomembranes In: Packer L. and Douce R. (eds.) *Methods in Enzymology*, vol 148 pp 350-382. Academic Press, London.

Maxwell Kate (2000), Chlorophyll fluorescence—a practical guide. *Journal of experimental botany vol.* 51 no 345. pp. 659-668.

*US. Pharmacopeia National Formulary* (1990), USP XXII, NP XVII, p. 1789, United States Pharmacopeial Convention Inc., Rockville, Md.

The invention claimed is:

1. A method for manufacture of an oral composition, the method comprising the steps of:
    mixing a purified active thylakoid extract with an orally-acceptable non-aqueous carrier, wherein the composition when ingested in a subject, has antioxidant and anti-inflammatory activity.

2. The method of claim 1, wherein the purified active thylakoid extract is present in an amount between 1 to 1000 mg.

3. The method of claim 1, wherein the carrier is present in an amount of 0.01% to 95% (w/w) of the total composition.

4. The method of claim 1, wherein the oral composition is a food supplement.

5. The method of claim 1, wherein the oral composition is a medication.

6. The method of claim 1, further comprising the step of: pressing said mixture to form a pellet.

7. The method of claim 6, wherein said pellet comprises from 200 to 300 mg of purified active thylakoid extract.

8. The method of claim 1, further comprising the step of: encapsulating said mixture in a capsule.

9. The method of claim 8, wherein said capsule comprises from 200 to 300 mg of purified active thylakoid extract.

10. The method of claim 1, further comprising the step of: mixing the oral composition with a food component to form a food composition, wherein said oral composition prevents oxidative damages to the food component of the food composition.

\* \* \* \* \*